(12) United States Patent
Wu

(10) Patent No.: US 11,064,896 B2
(45) Date of Patent: Jul. 20, 2021

(54) NON-INVASIVE BLOOD PRESSURE MEASURING APPARATUS AND MEASURING METHOD THEREOF

(75) Inventor: Xiaoguang Wu, Shenzhen (CN)

(73) Assignee: SHENZHEN RAYCOME HEALTH TECHNOLOGY CO., LTD., Shenzhen (CN)

(*) Notice: Subject to any disclaimer, the term of this patent is extended or adjusted under 35 U.S.C. 154(b) by 776 days.

(21) Appl. No.: 13/814,609

(22) PCT Filed: May 17, 2011

(86) PCT No.: PCT/CN2011/000866
§ 371 (c)(1),
(2), (4) Date: Feb. 6, 2013

(87) PCT Pub. No.: WO2012/016421
PCT Pub. Date: Feb. 9, 2012

(65) Prior Publication Data
US 2013/0138001 A1    May 30, 2013

(30) Foreign Application Priority Data
Aug. 6, 2010 (CN) .......................... 201010247968.6

(51) Int. Cl.
*A61B 5/022* (2006.01)
*A61B 5/0235* (2006.01)
(Continued)

(52) U.S. Cl.
CPC .......... *A61B 5/02233* (2013.01); *A61B 5/024* (2013.01); *A61B 5/0235* (2013.01);
(Continued)

(58) Field of Classification Search
CPC .................... A61B 5/02225; A61B 5/02125
See application file for complete search history.

(56) References Cited

U.S. PATENT DOCUMENTS 4,271,843 A * 6/1981 Flynn ................. A61B 5/02225
600/494
4,730,621 A * 3/1988 Stott ...................... A61B 5/025
600/480
(Continued)

FOREIGN PATENT DOCUMENTS

CN    1778269     5/2006
CN    1868399    11/2006
(Continued)

*Primary Examiner* — Rajeev P Siripurapu
*Assistant Examiner* — Michael A Catina
(74) *Attorney, Agent, or Firm* — Bayramoglu Law Offices LLC

(57) ABSTRACT

A non-invasive blood pressure measuring apparatus includes a host provided with a microprocessor coupled with an air pressure sensor. A pressurized cuff is an inflatable cuff with a gas tube connected with the air pressure sensor, and fastened to a body portion where user's artery blood flow can be blocked completely after air inflation. A pulse wave detector is fixed at a downstream position of the pressurized cuff according to the artery blood flow direction. The microprocessor performs a real-time process to several pulse wave amplitudes detected by the pulse wave detector during the course of slow increase from zero and the corresponding pressures of the pressurized cuff to determine a systolic pressure; and the microprocessor performs a real-time process to several pulse delay periods which are the delay periods between the pulse waves and the corresponding pressure AC signals during the course of variable delay periods to relatively constant delay periods and the corresponding pressures of the pressurized cuff to determine a diastolic pressure.

6 Claims, 3 Drawing Sheets

(51) Int. Cl.
*A61B 5/024* (2006.01)
*A61B 5/00* (2006.01)

(52) U.S. Cl.
CPC .......... *A61B 5/02225* (2013.01); *A61B 5/742* (2013.01); *A61B 5/7475* (2013.01); *A61B 5/72* (2013.01)

(56) References Cited

U.S. PATENT DOCUMENTS

| | | | | |
|---|---|---|---|---|
| 5,277,187 | A * | 1/1994 | Pillsbury ............ | A61B 5/02141 600/490 |
| 5,680,870 | A * | 10/1997 | Hood, Jr. ........... | A61B 5/02116 600/495 |
| 7,826,890 | B1 * | 11/2010 | Winchester, Jr. .... | A61B 5/0059 600/407 |
| 2002/0147402 | A1 * | 10/2002 | Nitzan ................. | A61B 5/021 600/494 |
| 2006/0155205 | A1 * | 7/2006 | Sotos ................... | A61B 5/4806 600/529 |
| 2007/0112259 | A1 * | 5/2007 | Tateda ............... | A61B 5/02007 600/310 |
| 2008/0033310 | A1 * | 2/2008 | Yu ........................ | A61B 5/0225 600/493 |

FOREIGN PATENT DOCUMENTS

| | | |
|---|---|---|
| CN | 201150533 | 11/2008 |
| CN | 101912259 | 12/2010 |
| EP | 0997102 | 5/2000 |
| JP | 7-241278 | 9/1995 |

* cited by examiner

NON-INVASIVE BLOOD PRESSURE MEASURING APPARATUS AND MEASURING METHOD THEREOF

TECHNICAL FIELD

The present invention relates to blood pressure measuring apparatuses, and more particularly, to a non-invasive blood pressure measuring apparatus and measuring method thereof.

BACKGROUND

Blood pressure is one of the major medical parameters of human beings. Non-invasive blood pressure measurement is the most commonly used method of blood pressure check, including Korotkoff sound stethoscopy applied in a mercury sphygmomanometer and oscillometric method applied in most of electronic sphygmomanometers. Korotkoff sound stethoscopy is a simple method, and the disadvantage is that different people may get different measurement results, sometimes the difference is very significant, and the main reasons are: 1) the discontinuity of heartbeat can cause a mercury drop height to have an unavoidable error between two consecutive heartbeats; 2) when the blood flow is merely a trickle of flow, Korotkoff sound is not necessarily produced so that a user is unable to determine an emergence time of the characteristic sound while listening; 3) observing a mercury manometer often have an visual error while listening; 4) Identification of an emergence time of the characteristic sound while listening is relative to skill and proficiency; 5) pressure relief speed is likely to deviate from international standards for about 3~5 mmHg/sec to produce an error. Oscillometric method is a state-of-the-art electronic measurement method, the systolic and diastolic blood pressure are estimated based on the average pressure and the empirical coefficient to cause relatively large individual differences; the discontinuity of heartbeat also leads gasbag pressure drop between two consecutive heartbeats to produce an error; body movement, cuff vibration, gas tube vibration, gas tube rigidity and pressure release speed will affect the correctness of the measurement results.

SUMMARY

A technical problem to be solved by the present invention is to provide an improved non-invasive blood pressure measuring apparatus to compensate for the defects of the existing technology.

Another technical problem to be solved by the present invention is to provide an improved non-invasive blood pressure measuring method.

The present invention determines a systolic blood pressure and a diastolic blood pressure in blood pressure by a noninvasive way on the basis of the detected change information of the pulse wave. The pulse wave is a fluctuation generated by periodic expansion and contraction of the aortic root through the vessel wall to be spread outwards. The periodic expansion and contraction of the aortic root is synchronized with the periodic expansion and contraction of the heart.

The above-mentioned technical problems can be solved through the following technical solutions.

A non-invasive blood pressure measuring apparatus includes a host having a microprocessor coupled to an air pressure sensor, a pressurized cuff coupled to the air pressure sensor and being an inflatable cuff with a gas tube, and the pressurized cuff is fastened to a body portion where user's artery blood flow is blocked completely after air inflation. Wherein the non-invasive blood pressure measuring apparatus further includes a pulse wave detector connected with the host, the pulse wave detector is fixed at a downstream position of the pressurized cuff according to the artery blood flow direction, and the pulse wave detector is used to detect changes of the pulse wave and senses in real-time changes in the blood flow pulse generated by the pressure variation of the pressurized cuff;

wherein the microprocessor processes in real-time a plurality of pulse wave amplitudes detected by the pulse wave detector during the course of slow increase from zero and the corresponding pressure in the pressurized cuff to thereby determine the systolic pressure, based on the amplitudes of the pulse wave near the systolic pressure substantially showing a linear variation; the microprocessor performs a real-time process to several pulse delay periods which are the pulse delay periods between the pulse waves and the corresponding AC pressure signals during the course of variable pulse delay periods to relatively constant pulse delay periods and the corresponding pressures of the pressurized cuff to thereby determine the diastolic pressure, based on the time characteristic of the pulse delay periods between the pulse wave and the corresponding AC air pressure signals near the diastolic pressure.

Further, the pulse wave detector is a pressure-sensing pulse wave detector or a photoelectric sensing pulse wave detector.

Further, the host includes a pulse wave signal processing circuit, an air pressure signal processing circuit, an inflator pump motor control circuit, an air release solenoid valve control circuit, an interactive interface, an inflator pump, a small hole air release valve, an air release solenoid valve respectively coupled to the microprocessor, the pulse wave signal processing circuit is coupled with the pulse wave detector, and an output of the air pressure sensor is coupled to an input of the air pressure signal processing circuit, a motor of the inflator pump is coupled to the inflator pump motor control circuit, and the air release solenoid valve is coupled to the air release solenoid valve control circuit.

Further, the pulse wave signal processing circuit includes a pulse wave signal amplifier and a pulse wave signal ADC, an input of the pulse wave signal ADC (Analog-to-Digital Converter) is coupled to the pulse wave signal amplifier, and an output of the pulse wave signal ADC is coupled to the microprocessor or integrated in the microprocessor; the air pressure signal processing circuit includes the air pressure sensor disposed in the host, an air pressure signal amplifier coupled to the air pressure sensor, and the air pressure signal ADC, an input of the air pressure signal ADC is coupled to the air pressure signal amplifier, and an output of the air pressure signal ADC is coupled to the microprocessor or integrated in the microprocessor.

Preferably, the host further includes a pressurized cuff port connected with the pressurized cuff and a pulse wave detector socket coupled with the pulse wave detector, the pressurized cuff port is connected to an input of the air pressure sensor, and the pulse wave detector socket is coupled to an input of the pulse wave signal processing circuit.

Further, the air pressure signal amplifier is a dual channel parallel air pressure signal amplifier consisting of an air pressure signal AC amplifier and an air pressure signal DC amplifier, the air pressure signal AC amplifier is used to amplify AC air pressure signals corresponding to the fluctuation information of the air pressure in the pressurized cuff under the action of the blood flow pulse, and the air pressure signal DC amplifier is used to amplify DC air pressure signals corresponding to the air pressure information in the pressurized cuff.

Further, the air pressure signal ADC includes an AC air pressure signal ADC and a DC air pressure signal ADC, an input of the AC air pressure signal ADC is coupled to the air pressure signal AC amplifier, and an output of the AC air pressure signal ADC is coupled to the microprocessor or integrated in the microprocessor; and an input of the DC air pressure signal ADC is coupled to the air pressure signal DC amplifier, and an output of the DC air pressure signal ADC is coupled to the microprocessor or integrated in the microprocessor.

Further, the pressure-sensing pulse wave detector includes a pressure-sensing chip, a pulse wave signal lead wire coupled with the pressure-sensing chip, a cushion is disposed on an outer surface of the pressure-sensing pulse wave detector. When the pressure-sensing pulse wave detector is placed on the skin surface where the arteries is located, the periodic fluctuations of the skin surface is generated due to the periodic fluctuations of the artery blood vessel, and the pressure-sensing chip is squeezed by the cushion to generate a periodic piezoelectric signals, or to cause periodic resistance changes on the pressure sensing chip. The photoelectric sensing pulse wave detector includes a light emitter and a light receiver, a first power supply connected with the light emitter, a light emission signal lead wire, a second power supply connected with the light receiver, and a light receiving signal lead wire. When the photoelectric pulse wave detector is placed on the skin surface where the arteries is located, the periodic changes of absorption of the light emitted by the light emitter in the photoelectric pulse wave detector in a detected position is caused due to the periodic fluctuations of the artery blood vessel, and an electric signal pulse corresponding to the arterial blood flow pulse can be obtained by the light receiver in the photoelectric pulse wave detector detecting scattered lights or transmitted lights via the flow of blood after absorption.

The interactive interface is a human-computer interaction interface including a keyboard and a monitor therein.

The non-invasive blood pressure measuring method of the present invention can be solved through the following technical solutions.

The non-invasive blood pressure measuring method includes the steps of:

Step One:
the pressurized cuff is fastened to a body portion where user's artery blood flow is blocked completely after air inflation, the pulse wave detector is thereafter fixed at the downstream position of the pressurized cuff according to the artery blood flow direction;

Step Two:
after a start key on the keyboard of the host is pressed, the inflator pump motor is wired in to a power supply, and then, the inflator pump motor begins to inflate the pressurized cuff, and a pressure in the pressurized cuff is slowly increased from zero until an output signal from the pressure-sensing pulse wave detector is zero, that is, the arterial blood flow is completely blocked, thereafter, the inflator pump motor is switched off to stop inflation.

Step Three:
with the air release solenoid valve being closed, when a small hole air release valve is opened to slowly release the air, the pressure in the pressurized cuff is slowly decreased, and the signals detected by the pressure-sensing pulse wave detector are slowly increased from zero until the pressure in the pressurized cuff is less than the diastolic pressure, during the course of air release, the air pressure pulse signals and the signals detected by the pressure-sensing pulse wave detector are respectively amplified and performed an analog-to-digital conversion into the microprocessor to be recorded and analyzed;

the microprocessor processes in real-time a plurality of pulse wave amplitudes detected by the pulse wave detector during the course of slow increase from zero and the corresponding pressure in the pressurized cuff to determine the systolic pressure, based on the amplitudes of the pulse wave near the systolic pressure substantially presenting a linear variation;

the microprocessor performs a real-time process to several pulse delay periods which are the pulse delay periods between the pulse waves and the corresponding AC pressure signals during the course of variable pulse delay periods to relatively constant pulse delay periods and the corresponding pressures of the pressurized cuff to determine the diastolic pressure, based on the time characteristic of the pulse delay periods between the pulse wave and the corresponding AC air pressure signals near the diastolic pressure;

Step Four:
the air release solenoid valve is opened to quickly deflate the air, the pressure in the pressurized cuff is quickly dropped to zero, and a monitor shows the measurement results of the systolic pressure and the diastolic pressure;

Step Five:
press the power key on the keyboard to turn off the host and finish the measurements.

Further, the systolic pressure is determined by the following formula:

$$Pss0=(H2*Pss2-H1*Pss1)/(H2-H1),$$

in the formula:
Pss0 is an accurate systolic pressure, when the pressurized cuff is pss0, the blood flow is exactly transited from a completely blocked state to a gradual flow state, at this time, the amplitude of the pulse wave H0 is zero;

H2 is the amplitude of the pulse wave when the pressure of the pressurized cuff is Pss2; and H1 is the amplitude of the pulse wave when the pressure of the pressurized cuff is Pss1. the formula of the systolic pressure basically presents a linear variation based on the amplitudes of the pulse wave near the systolic pressure when the pressure in the pressurized cuff is changed, this is, (Pss2-Pss0): H2=(Pss1-Pss0): H1, the above formulae are actually equal but just different in an expression form.

Further, in step 3, the diastolic pressure is determined by the following steps:

(3.1) the characteristic curve of the pulse delay periods between the pulse wave consisting of at least consecutive five dots data near the diastolic pressure and the corresponding AC air pressure signal is measured, wherein the pressure of the pressurized cuff, and the pulse delay periods between the pulse wave and the corresponding AC air pressure signals in at least continuous three dots data substantially present a linear variation, the relation curve is a slant line, and the following first relational expression is established:

$$(Psz3-Psz0): (T3-T0)=(Psz2-Psz0): (T2-0)=(Psz1-Psz0): (T1-T0);$$

in addition, the pressure of the pressurized cuff, and the pulse delay periods between the pulse wave and the corresponding AC air pressure signals in at least continuous two dots data substantially presents a fixed value, the relation curve is a horizontal line, and the following second and third relational expressions are established:

$$Psz0 > PszA > PszB;$$

$$T0 = (TA + TB)/2;$$

(3.2) the diastolic pressure is determined by an intersection point between the slant line and the horizontal line in the time characteristic curves, in the first and second relational expressions, Psz0 is an accurate diastolic pressure, and this point is an intersection point between the above slant line and the horizontal line; in the third relational expression, T0 is an accurate delay time in the diastolic pressure point.

Further, the body portion where user's artery blood flows blocked completely after air inflation, includes an elbow portion, a wrist portion, a finger portion, a leg portion and an ankle portion.

Comparing with the prior arts, the beneficial effects of the present invention are described as follow: noncontinuous events are transformed into continuous measurements in the present invention, on the one hand, based on the measured pulse wave amplitude substantially presenting a linear change near the systolic blood pressure, judgment of Korotkoff sound starting from scratch is replaced to avoid an inevitable possible error caused by the discontinuity of heartbeat, thereby accurately measuring a systolic blood pressure in blood pressure; on the other hand, based on the time characteristic of the pulse delay periods between the pulse wave and the corresponding AC air pressure signals near the diastolic pressure, judgment of Korotkoff sound starting from scratch is replaced to avoid an inevitable possible error caused by the discontinuity of heartbeat, thereby accurately measuring a diastolic blood pressure in blood pressure.

DETAILED DESCRIPTION OF THE PREFERRED EMBODIMENTS

Embodiments of the present invention will be explained below in detail with reference to the accompanying drawings.

Figure 1:
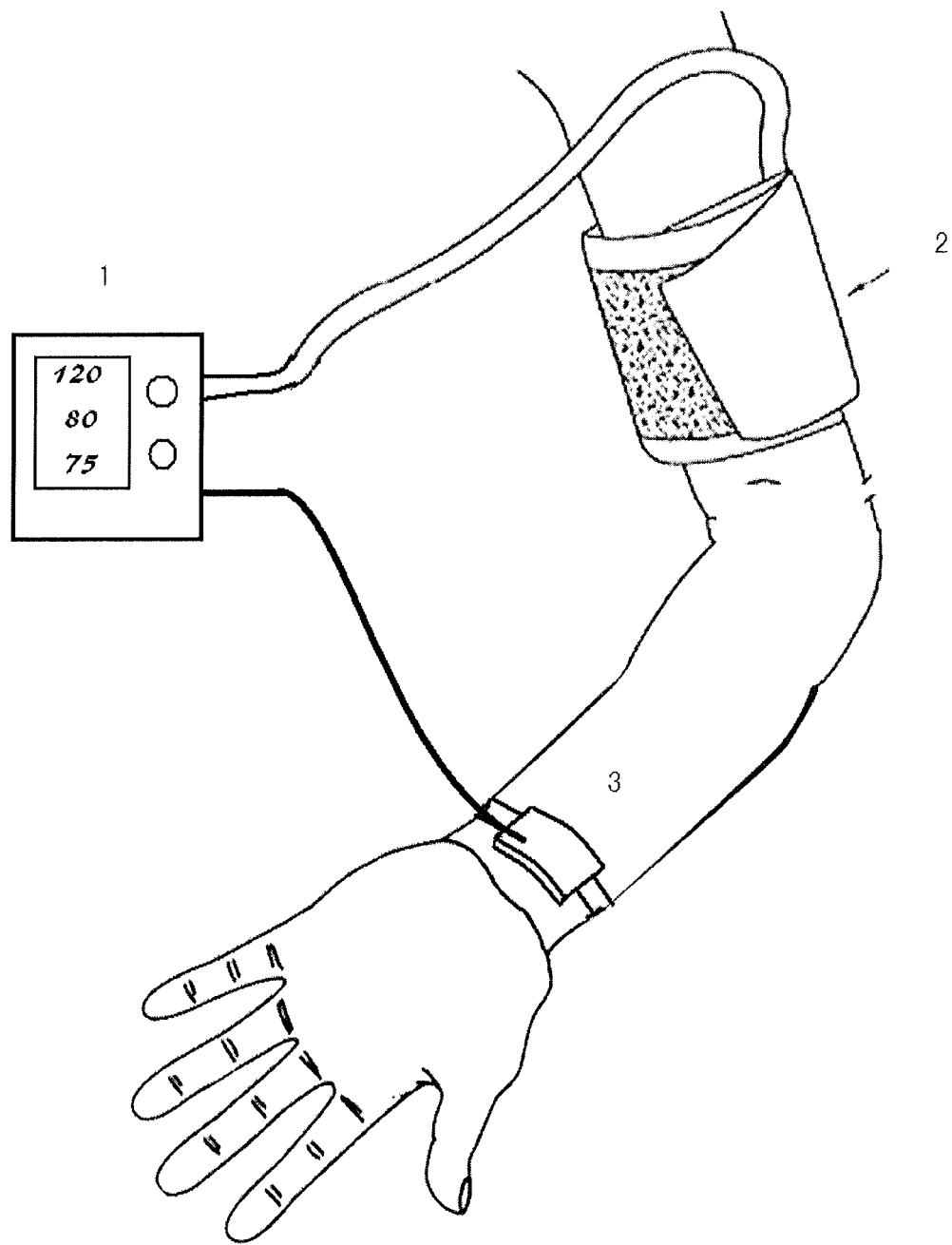
FIG. 1 is a schematic view of a non-invasive blood pressure measuring apparatus in accordance with an embodiment of the present invention in a use state.
Figure 2:
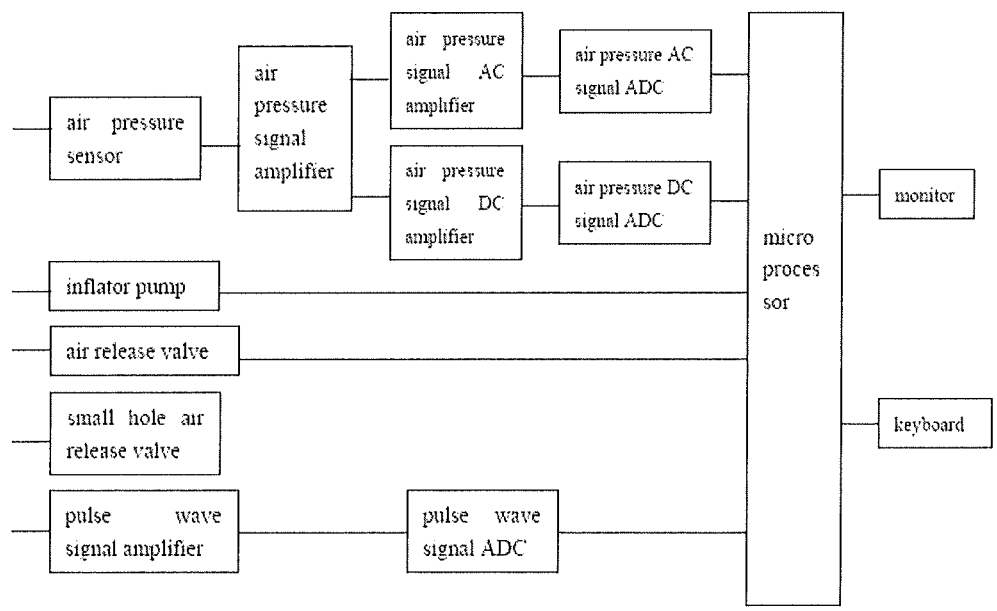
FIG. 2 is a component block diagram of a host of the non-invasive blood pressure measuring apparatus.
Figure 3:
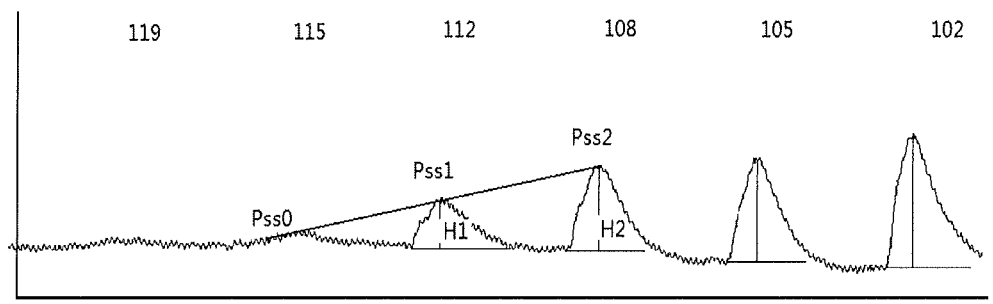
FIG. 3 is a basically and linearly changed view of a pulse wave amplitude near a systolic pressure relative to a pressure change of a pressurized cuff in the embodiment of the present invention.
Figure 4:
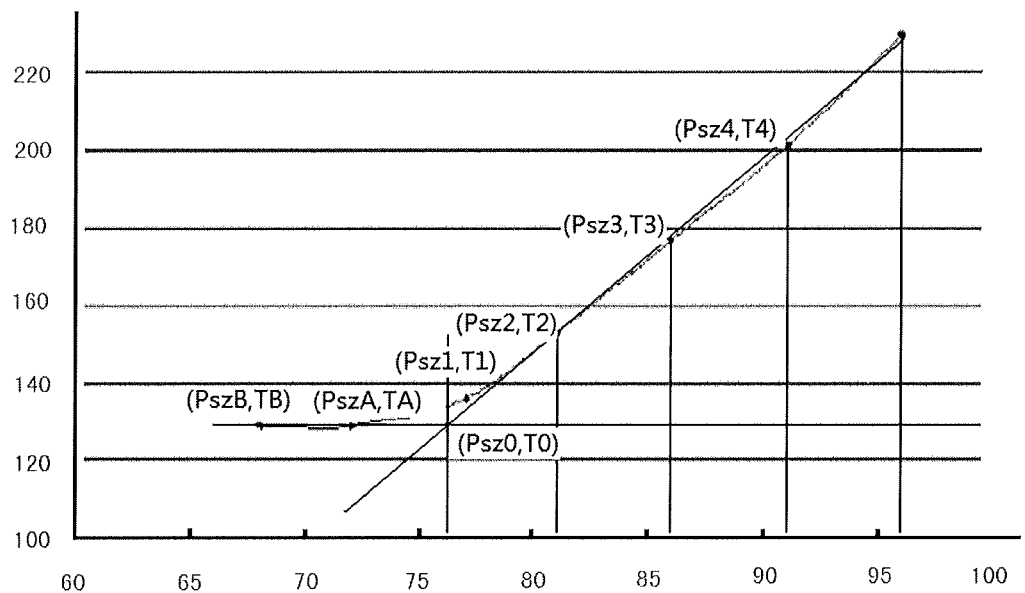
FIG. 4 is a changed view of a pulse wave delay periods before and after a diastolic pressure relative to a pressure change of a pressurized cuff in the embodiment of the present invention.

Referring to FIGS. 1 to 4, a non-invasive blood pressure measuring apparatus and a measuring method in accordance with the embodiment of the present invention includes a host 1, a pressurized cuff 2 (an arm-band) and a pressure-sensing pulse wave detector 3 respectively connected with the host 1. The pressurized cuff 2 is an inflatable cuff with a gas tube, which is connected with a pressurized cuff port disposed on the host 1 and fastened to a body portion where user's artery blood flow can be blocked completely after air inflation. A pressure-sensing pulse wave detector 3 is fixed at a downstream position of the pressurized cuff 2 according to the artery blood flow direction and coupled with a pulse wave detector socket disposed on the host 1. The pressure-sensing pulse wave detector 3 is used to detect a change of the pulse wave and sense in real-time the changes in the blood flow pulse generated by the pressure variation of the pressurized cuff 2.

The host 1 includes a microprocessor, a pulse wave signal processing circuit, an air pressure signal processing circuit, an inflator pump motor control circuit, an air release solenoid valve control circuit, an interactive interface, an air pressure sensor, an inflator pump, a small hole air release valve, an air release solenoid valve, a pulse wave detector socket connected with the pressure-sensing pulse wave detector 3, and the pressurized cuff port connected with the pressurized cuff 2 by the gas tube. The pulse wave signal processing circuit, the air pressure signal processing circuit, the inflator pump motor control circuit, the air release solenoid valve control circuit, the interactive interface, the air pressure sensor, the inflator pump, the small hole air release valve, and the air release solenoid valve are respectively coupled with the microprocessor. The pulse wave detector socket is coupled to an input of the pulse wave signal processing circuit, and the pressurized cuff port is connected with the air pressure sensor. An output of the air pressure sensor is coupled to an input of the air pressure signal processing circuit. A motor of the inflator pump is coupled to the inflator pump motor control circuit. The air release solenoid valve is coupled to the air release solenoid valve control circuit.

The pulse wave signal processing circuit includes a pulse wave signal amplifier and a pulse wave signal ADC (Analog-to-Digital Converter). An input of the pulse wave signal ADC is coupled to the pulse wave signal amplifier, and an output of the pulse wave signal ADC is coupled to the microprocessor. The pulse wave signal ADC is integrated within the microprocessor.

The air pressure signal processing circuit includes the air pressure sensor disposed in the host 1, an air pressure signal amplifier coupled to the air pressure sensor, and the air pressure signal ADC. An input of the air pressure signal ADC is coupled to the air pressure signal amplifier, and an output of the air pressure signal ADC is coupled to the microprocessor. The air pressure signal ADC may be integrated within the microprocessor.

The air pressure signal amplifier is a dual channel parallel air pressure signal amplifier consisting of an air pressure signal AC amplifier and an air pressure signal DC amplifier. The air pressure signal AC amplifier is used to amplify AC air pressure signals corresponding to the fluctuation information of the air pressure in the pressurized cuff 2 under the action of the blood flow pulse, and the air pressure signal DC amplifier is used to amplify DC air pressure signals corresponding to the air pressure information in the pressurized cuff 2.

The air pressure signal ADC includes an air pressure AC signal ADC and an air pressure DC signal ADC. An input of the air pressure AC signal ADC is coupled to the air pressure signal AC amplifier, and an output of the air pressure AC signal ADC is coupled to the microprocessor. An input of the air pressure DC signal ADC is coupled to the air pressure signal DC amplifier, and an output of the air pressure DC signal ADC is coupled to the microprocessor.

The interactive interface is a human-computer interaction interface including a keyboard and a monitor therein.

The measuring method of the embodiment of the non-invasive blood pressure measuring apparatus includes the following steps in turn:

Step One:

the pressurized cuff 2 is firstly connected with the pressurized cuff port disposed on the host 1 by the gas tube, and then fastened to the body portion such as an arm where user's artery blood flow can be blocked completely after air inflation. The pressure-sensing pulse wave detector 3 is thereafter fixed at the downstream position of the pressurized cuff 2 according to the artery blood flow direction and coupled with the pulse wave detector socket disposed on the host 1.

Step Two:

After a start key on the keyboard of the host 1 is pressed, the inflator pump motor is wired in to a power supply, and then, the inflator pump motor begins to inflate the pressurized cuff 2, and a pressure in the pressurized cuff 2 is slowly increased from zero until an output signal from the pressure-sensing pulse wave detector 3 is zero, that is, the arterial blood flow is completely blocked. Thereafter, the inflator pump motor is switched off to stop inflation.

Step Three:

with the air release solenoid valve being closed, when a small hole air release valve on the host is opened to slowly release the air, the pressure in the pressurized cuff 2 is slowly decreased, and the signals detected by the pressure-sensing pulse wave detector 3 are slowly increased from zero until the pressure in the pressurized cuff 2 is less than the diastolic pressure, during the course of air release, the air pressure pulse signals and the signals detected by the pressure-sensing pulse wave detector 3 are respectively amplified and performed an analog-to-digital conversion into the microprocessor to be recorded and analyzed.

The microprocessor processes in real-time a plurality of pulse wave amplitudes detected by the pulse wave detector 3 during the course of slow increase from zero and the corresponding pressure in the pressurized cuff 2, based on the amplitudes of the pulse wave near the systolic pressure substantially showing a linear variation. The systolic pressure is determined by the following formula:

$$Pss0=(H2*Pss2-H1*Pss1)/(H2-H1) \quad (1);$$

in the formula (1):

Pss0 is an accurate systolic pressure, when the pressurized cuff 2 is pss0, the blood flow is exactly transited from a completely blocked state to a gradual flow state, at this time, the amplitude of the pulse wave H0 is zero;

H2 is the amplitude of the pulse wave when the pressure of the pressurized cuff 2 is Pss2;

H1 is the amplitude of the pulse wave when the pressure of the pressurized cuff 2 is Pss1;

the microprocessor performs a real-time process to several pulse delay periods which are the pulse delay periods between the pulse waves and the corresponding AC pressure signals during the course of variable pulse delay periods to relatively constant pulse delay periods and the corresponding pressures of the pressurized cuff to determine the diastolic pressure, based on the time characteristic of the pulse delay periods between the pulse wave and the corresponding AC air pressure signals near the diastolic pressure;

3.1) the characteristic curve of the pulse delay periods between the pulse wave consisting of at least consecutive five dots data near the diastolic pressure and the corresponding AC air pressure signal is measured, wherein the pressure of the pressurized cuff, and the pulse delay periods between the pulse wave and the corresponding AC air pressure signals in at least continuous three dots data substantially present a linear variation, the relation curve is a slant line, and the following relational expression is established:

$$(Psz3-Psz0):(T3-T0)=(Psz2-Psz0):(T2-T0)=(Psz1-Psz0):(T1-T0); \quad (3).$$

In addition, the pressure of the pressurized cuff, and the pulse delay periods between the pulse wave and the corresponding AC air pressure signals in at least continuous two dots data substantially present a fixed value, the relation curve is a horizontal line, and then the following relational expression is established:

$$Psz0>PszA>PszB; \quad (4);$$

$$T0=(TA+TB)/2; \quad (5).$$

3.2) the diastolic pressure is determined by an intersection point between the slant line and the horizontal line in the time characteristic curves, in the relational expression (3) and (4), Psz0 is an accurate diastolic pressure, and this point is an intersection point between the above slant line and the horizontal line; in the relational expression (5), T0 is an accurate delay time in the diastolic pressure point.

Step Four:

The air release solenoid valve is opened and the air is quickly released, the pressure in the pressurized cuff is quickly dropped to zero, and the monitor shows the measurement results of the systolic pressure and the diastolic pressure;

Step Five:

press the power key on the keyboard to turn off the host 1 and finish the measurements.

The present invention may be embodied in other forms without departing from the spirit or novel characteristics thereof. The embodiments disclosed in this application are to be considered in all respects as illustrative and not limitative. The scope of the invention is indicated by the appended claims rather than by the foregoing description; and all changes which come within the meaning and range of equivalency of the claims are intended to be embraced therein.

What is claimed is:

1. A non-invasive blood pressure measuring apparatus, comprising: a host comprising a microprocessor coupled to an air pressure sensor;

a pressurized cuff coupled to the air pressure sensor, wherein the pressurized cuff is an inflatable cuff with a gas tube, wherein the pressurized cuff generates changes in a blood flow pulse via, a pressure variation of the pressurized cuff; and a pulse wave detector connected with the host, wherein the pulse wave detector detects changes of a pulse wave and senses, in real-time, changes in the blood flow pulse generated by the pressure variation of the pressurized cuff, wherein the microprocessor processes, in real-time, a plurality of pulse wave amplitudes detected by the pulse wave detector and the pressure variation of the pressurized cuff corresponding to the plurality of pulse wave amplitudes, the microprocessor performs a real-time process on pulse delay periods between the plurality of pulse wave amplitudes and an AC air pressure signal component corresponding to the pressure variation of the pressurized cuff, wherein a pulse wave amplitude of the plurality of pulse wave amplitudes corresponds with the AC pressure signal component measured from the pressure variation of the pressurized cuff for each blood flow pulse, generating a time characteristic curve wherein a time characteristic curve comprises:

the pulse delay periods between the pulse wave amplitude consisting of at least consecutive five data points near a diastolic pressure and the AC air pressure signal is measured, wherein pressures of the pressurized cuff and the pulse delay periods between the pulse wave and the AC air pressure signal in at least continuous three data points present a linear variation a first relation curve is a slant line, and a first relational expression of $(Psz3-Psz0): (T3-T0)=(Psz2-Psz0): (T2-T0)=(Psz1-Psz0): (T1-T0)$ is established, Wherein Psz0 is a diastolic pressure point, Psz1 is a cuff pressure associated with a delay time T1, Psz2 is a cuff pressure associated with a delay time T2, Psz3 is a cuff pressure associated with a delay time T3 and T0 is a delay time at the diastolic pressure point Psz0 the pressures of the pressurized cuff and the pulse delay periods between the pulse wave and the AC air pressure signal in at least consecutive two data points, wherein the pulse delay periods are presented as fixed values while the pressures of the pressurized cuff vary, a second relation curve is a horizontal line, and a second relational expression of Psz0>PszA/PszB is established, and a third relational expression of T0=(TA+TB)/2 is established, and an intersection point between the slant line and the horizontal line in the time characteristic curve, wherein Psz0 is the diastolic pressure and is the intersection point, PszA and PszB are consecutive pressures of the pressurized cuff near the diastolic pressure;

T0 is the delay time at the diastolic pressure point, and TA and TB are delay times near T0 on the horizontal line, and wherein the pulse wave detector is a photoelectric sensing pulse wave detector which includes a light emitter, a light receiver, a first power supply connected with the light emitter a light emission signal lead wire, a second power supply connected with the light receiver, and a light receiving signal lead wire; when the photoelectric pulse wave detector is placed on a skin surface where arteries are located, periodic changes of absorption of light emitted by the light emitter in the photoelectric pulse wave detector in a detected position is caused due to periodic fluctuations of an artery blood vessel, and an electric signal pulse corresponding to an arterial blood flow pulse is obtained by using the light receiver in the photoelectric pulse wave detector to detect scattered lights or transmitted lights absorbed by blood flow wherein the microprocessor determines a diastolic pressure based on the time characteristic curve of the pulse delay periods between the pulse wave and the corresponding AC air pressure signal; and a monitor connected to the microprocessor to display the diastolic pressure and a systolic pressure.

2. The non-invasive blood pressure measuring apparatus as claimed in claim 1, wherein the host comprises a pulse wave signal processing circuit, an air pressure signal processing circuit, an inflator pump motor control circuit, an air release solenoid valve control circuit, an interactive interface, an inflator pump, a hole air release valve, an air release solenoid valve respectively coupled to the microprocessor, wherein the pulse wave signal processing circuit is coupled with the pulse wave detector, an output of the air pressure sensor is coupled to an input of the air pressure signal processing circuit, a motor of the inflator pump is coupled to the inflator pump motor control circuit, and the air release solenoid valve is coupled to the air release solenoid valve control circuit.

3. The non-invasive blood pressure measuring apparatus as claimed in claim 2, wherein the pulse wave signal processing circuit comprises:

a pulse wave signal amplifier and a pulse wave signal analog to digital converter, wherein an input of the pulse wave signal analog to digital converter coupled to the pulse wave signal amplifier, and an output of the pulse wave signal analog to digital converter coupled to the microprocessor or integrated in the microprocessor;

the air pressure signal processing circuit which comprises the air pressure sensor disposed in the host, an air pressure signal amplifier coupled to the air pressure sensor, and the air pressure signal analog to digital converter, an input of the air pressure signal analog to digital converter coupled to the air pressure signal amplifier, and an output of the air pressure signal analog to digital converter coupled to the microprocessor or integrated within the microprocessor.

4. The non-invasive blood pressure measuring apparatus as claimed in claim 3, wherein the host further comprises a pressurized cuff port connected with the pressurized cuff and a pulse wave detector socket coupled with the pulse wave detector, wherein the pressurized cuff port is connected to an input of the air pressure sensor, and the pulse wave detector socket is coupled to an input of the pulse wave signal processing circuit.

5. The non-invasive blood pressure measuring apparatus as claimed in claim 4, wherein the air pressure signal amplifier is a dual channel parallel air pressure signal amplifier consisting of an air pressure signal AC amplifier and an air pressure signal DC amplifier, wherein the air pressure signal AC amplifier is used to amplify, the AC air pressure signal corresponding to the pressure variation of the air pressure in the pressurized cuff under an action of the blood flow pulse, and the air pressure signal DC amplifier is used to amplify DC air pressure signals corresponding to air pressure information in the pressurized cuff.

6. A non-invasive blood pressure measuring method, comprising:

fastening a pressurized cuff and a pulse wave detector to a body portion of a user;

connecting, after a start key on a keyboard of a host is pressed, an inflator pump motor in to a power supply, and then, the inflator pump motor begins to inflate the pressurized cuff with air, and slowly increasing a pressure in the pressurized cuff from zero until an output signal from a pressure-sensing pulse wave detector is zero, such that an arterial blood flow is completely blocked, and thereafter, the inflator pump motor is switched off to stop inflation;

opening an air release solenoid valve to an air release position, such that a hole air release valve is opened to slowly release the air, and slowly decrease the pressure in the pressurized cuff, and slowly increase signals detected by the pressure-sensing pulse wave detector from zero until the pressure in the pressurized cuff is less than a diastolic pressure;

amplifying, during a course of air release, air pressure pulse signals measured from the pressurized cuff and the signals detected by the pressure-sensing pulse wave detector, respectively;

performing an analog-to-digital conversion on the signals detected by the pressure-sensing pulse wave detector and the air pressure signals into the microprocessor to be recorded and analyzed;

processing in real time, using the microprocessor, a plurality of pulse wave amplitudes detected by the pulse wave detector during a course of increase from zero and the pressure of the pressurized cuff corresponding to the plurality of pulse wave amplitudes:

performing a real-time process by the microprocessor on pulse delay periods between an amplitude of a pulse wave and a corresponding AC pressure signal and the pressures of the pressurized cuff corresponding to the pulse delay periods to determine the diastolic pressure, based on a time characteristic of the pulse delay periods between the amplitude of a pulse wave and an AC air pressure signal corresponding to a pressure variation of the pressurized cuff; and displaying, via a monitor connected to the microprocessor, the diastolic pressure and systolic pressure, wherein the systolic pressure is determined by the following formula: $Pss0=(H2*Pss2-H1*Pss1)/(H2-H1)$, in the formula, wherein $Pss0$ is a systolic pressure, when the pressurized cuff pressure is $Pss0$, a blood flow is transited from a completely blocked state to a gradual flow state, at this time, an amplitude of the pulse wave $H0$ is zero; and $H2$ is the amplitude of the pulse wave when the pressure of the pressurized cuff is $Pss2$, and $H1$ is the amplitude of the pulse wave when the pressure of the pressurized cuff is $Pss1$.

\* \* \* \* \*